United States Patent [19] [11] 4,039,837
Ohta et al. [45] Aug. 2, 1977

[54] METHOD OF MAKING TOMOGRAM AND APPARATUS

[75] Inventors: Sadayasu Ohta, Kyoto; Akio Yada, Uji; Keizo Inoue, Kyoto, all of Japan

[73] Assignee: Kabushiki Kaisha Morita Seisakusho, Kyoto, Japan

[21] Appl. No.: 702,299

[22] Filed: July 2, 1976

[30] Foreign Application Priority Data

Feb. 25, 1976 Japan .................................. 51-20455

[51] Int. Cl.² .............................................. A61B 6/02
[52] U.S. Cl. ................................. 250/445 T; 250/446
[58] Field of Search ............................ 250/445 T, 446

[56] References Cited
U.S. PATENT DOCUMENTS 3,737,660 6/1973 Ando et al. ...................... 250/445 T Primary Examiner—Alfred E. Smith
Assistant Examiner—T. N. Grigsby
Attorney, Agent, or Firm—Christensen, O'Connor, Garrison & Havelka

[57] ABSTRACT

Method and apparatus for making a tomogram according to this invention include one elongated support member supporting an X-ray tube and a film device in an opposed relation with each other at both ends thereof and one vertical shaft supporting the elongated support member thereon. Movement of the axis of the shaft along a desired curve results in the movement of an X-ray beam in the state of the X-ray beam intersecting the curve. In the meantime, an angle of rotation around the axis of the shaft is adjusted so as to maintain an angle of intersection of the X-ray beam with the curve at a predetermined angle. A film surface is moved relatively with respect to the X-ray beam so as to allow the beam to scan the film surface. The velocity of movement of the film surface is synchronized with the movement of the shaft. In the invention, the aforementioned movement of the shaft along the curve, the aforementioned angle of rotation of the shaft and the aforementioned movement of the film surface are respectively controlled or adjusted by digital signals.

11 Claims, 3 Drawing Figures

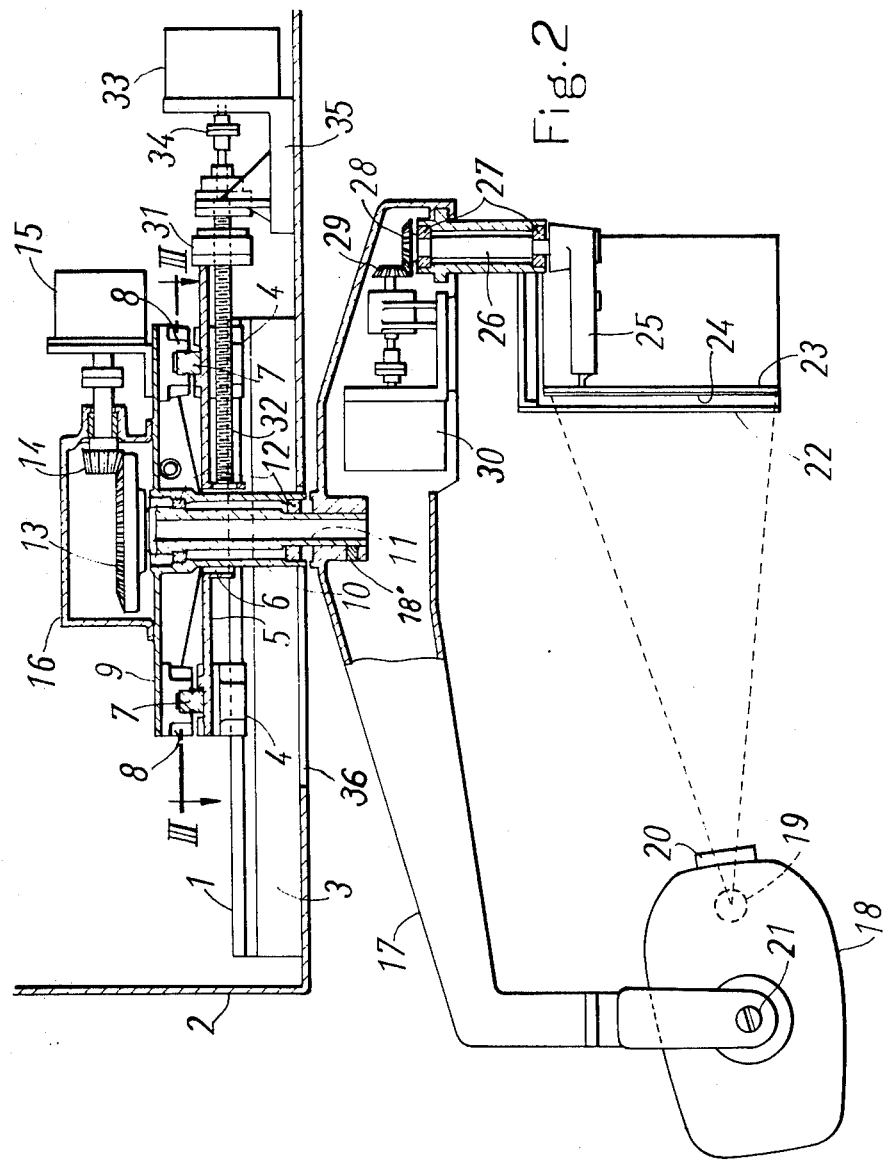

METHOD OF MAKING TOMOGRAM AND APPARATUS

BACKGROUND OF THE INVENTION

1. Field of the Invention

This invention relates to a novel method and apparatus for making a tomogram and particularly to a method and apparatus suitable for making a tomogram of the arrangement of teeth of a human being. 2. Description of the Prior Art In a typical method of making a tomogram, an X-ray tube is moved so that a long and narrow X-ray beam projected from the X-ray tube through a slit on a film device can move while the beam is intersecting a desired curve, namely, a curve defining the curved surface along which a tomogram is made. In this case, a relative position of the X-ray tube with respect to the film device is kept unchanged. And the film in the film device is moved relatively with respect to the beam so as to allow the beam to scan the film surface. As a result, an X-ray image along the curved surface defined by the desired curve is photographed on the film surface. When the desired curve is a dental arch curve, a tomogram of the dental arch is made on the film surface.

In the orthopantomography well known as a tomography of arrangement of teeth, the X-ray tube device travels along a composite curved path approximate to a parabola joining three arcs. Accordingly, in this case, a curve defining the curved surface along which a tomogram is made is also an approximate parabola. In the orthopantomography, the light and left molar portions each are approximated by one arc and an incisor portion is approximated by another arc. And in an elliptic tomography which is described in detail in U.S. Patent Specification No. 3,806,731, both the X-ray tube and film device are moved along an elliptic path. Accordingly, in this case, a curve defining the curved surface along which a tomogram is made is an elliptic curve.

But there is a substantial difference is dentition between individual persons. Dentition varies with races, sexes or ages, and statistically it is classified into a considerable number of types. For example, there is not a few cases where a dental arch is V-shaped or U-shaped, but irrespective of whether recourse is had to the orthopantomography or to the elliptic tomography in such a case, there is a nonegligible discrepancy between the shape of the path of X-ray tube -- hence the shape of a curve defining the curved surface along which a tomogram is made -- and the shape of an actual dental arch. In making a tomogram such a discrepancy brings about such substantial reductions in the quality of the resulting photograph -- blurring of the photograph -- as hamper a diagnosis or make it difficult.

SUMMARY OF THE INVENTION

Accordingly, an object of this invention is to make it possible an invariably clear and sharp tomogram in spite of varied differences between individual persons.

Another object of the invention is to make it possible to make a tomogram along any desired curved surface.

Still another object of the invention is to provide a method and apparatus for making a tomogram in which an X-ray tube travels along any desired path without the path for the X-ray tube being restricted to any specified shape.

The invention includes one elongated support member supporting an X-ray tube and a film device in an opposed relation with respect to each other at both ends thereof and one vertical shaft supporting the elongated support member thereon. According to the invention, the axis of the shaft is moved along any desired curve, with the result that a long and narrow X-ray beam which is projected from the X-ray tube on the film device is moved while intersecting the curve. While the X-ray beam is moving, an angle of intersection of the X-ray beam with the curve is kept always at a predetermined angle. Because of this, the angle of intersection is adjusted by turning the shaft around the axis thereof. On the other hand, an X-ray film in the film device is moved relatively with respect to an incident X-ray beam in the manner that the incident X-ray beam may scan the film surface, and the velocity of movement of the film is synchronized with the velocity at which the axis of the shaft travels along the curve. And in the invention, the movement of the shaft along the curve, rotation of the shaft around the axis thereof, and movement of the film surface in the manner described above are respectively controlled or adjusted by digital signals.

BRIEF DESCRIPTION OF THE DRAWINGS

The invention will be more fully understood from the following description taken with reference to the accompanying drawings in which:

FIG. 2 is a partial longitudinal sectional elevation of an apparatus for making a tomogram of arrangement of teeth shown in a preferred form of the invention.

DETAILED DESCRIPTION OF THE PREFERRED EMBODIMENT

Figure 1:
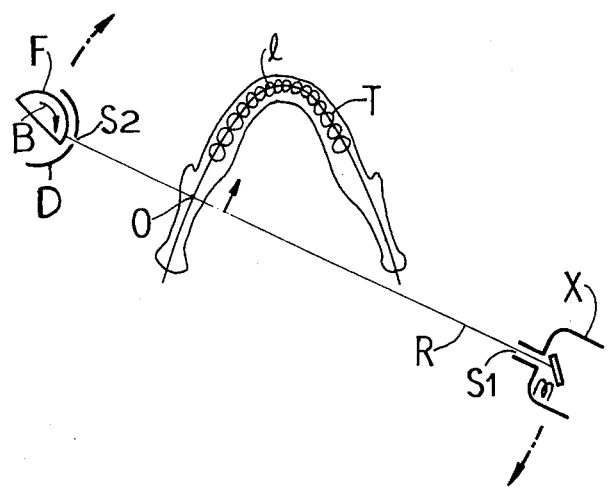
FIG. 1 is a diagram explaining the principle of an X-ray tomography.

A description will be taken of the principle of an apparatus for making a tomogram according to the invention with reference to FIG. 1. In the Figure, reference character $l$ designates a curve defining a curved surface along which a tomogram is made, and when a tomogram is made of the arrangement of teeth, the character $l$ designates a curve representative of the shape of a dental arch T. Reference character X designates an X-ray tube, in front of which a slit $S_1$ is provided. The X ray R irradiated from the X-ray tube X is narrowed down by the slit $S_1$ to an X-ray beam large in length and very small in width, and F designates an X-ray film inside a film device D, and a slit $S_2$ is provided in front of film F. The X-ray tube $X$ and film device D are provided in an opposed relation with each other at both ends of an elongated support member (not shown), and accordingly a relative positional relation between the two is kept unchanged, and the X-ray beam projected through the slit $S_1$ is always incident through the slit $S_2$. Conversely, the X-ray incident through the slit $S_2$ is limited to the X-ray beam projected through the slit $S_1$, and scattering X-ray beam is prevented by the slit $S_2$ from finding its way into the film device D.

When the X-ray beam is moved in the direction of a solid line arrow while it is intersecting the curve $l$ so that both X-ray tube X and film device D may keep their relative positional relation unchanged, the point of intersection O of X-ray beam with the curve $l$ moves along the curve $l$ together with the movement of the X-ray tube and film device D. In this connection, when the angle at which the X-ray beam intersects the curve

*l*, namely, the angle at which the X-ray beam intersects a tangent in contact with the curved *l* is kept at a predetermined angle at point of intersection O (generally kept in the manner that the X-ray beam intersects the tangent at right angles therewith) and, for example, when a film surface F is scanned by the X-ray beam by moving the film F stretched arund the surface of a driven drum at the velocity B synchronized with the velocity at which the point of intersection O of the projected X ray with the curve *l* is moved along the curve *l*, a tomogram along the curved surface defined by curve *l*, namely, a tomogram of arrangement of teeth is made on the film F. That is to say, if the velocity at which the point of intersection O is moved along the curve *l* and the velocity at which the film F is moved (both of which may be indicated in terms of either linear velocity or angular velocity) are indicated in terms of linear velocity, the linear velocity of movement of each point on the projected X ray which intersects the curve *l* at a predetermined angle and which moves while crossing the curve *l* is different at each point. Accordingly, if the film is fed at the velocity at which the linear velocity of film F bears a certain ratio to the linear velocity of the point of intersection O, namely if the film is fed at such velocity as that which the linear velocity of film F becomes linear velocity B made by multiplying the linear velocity of point of intersection O by a certain magnifying ratio (this ratio is that which is obtained by dividing a distance between X-ray source and the film F by a distance between the X-ray source and the point of intersection O), only the point of intersection O with the curve *l* out of each point on the projected X ray B moves in synchronism with the film surface F that travels at that velocity B and is in a relatively still relation with respect to the film surface F. Accordingly, the image at that point of intersection O -- more precisely speaking, a unit image having an area corresponding to a sectional area of X-ray beam -- is vividly photographed as a still image. In contrast thereto, because each point on the projected X ray other than the point of intersection O moved relatively with respect to the film surface F, the image gets blurred. After all, only the image of a plane section along the curved surface defined by the curve *l* is photographed on the film. And feed of film F, as described, is carried out by turning a drum around whose surface the film F is stretched. And chain line arrows indicating the film device D and X-ray source X in FIG. 1 indicate a direction of relative movement with respect to the point of intersection O incidental to the movement which the device D and source X make along the curve *l* at the point of intersection O. Furthermore, in the following description, the linear velocity of film F and X-ray source X is indicated merely as the velocity of movement.

According to the principle of the tomography described, it is necessary to make three kinds of control simultaneously in the form of 1) moving the X-ray tube and the film device in the manner that the projected X-ray travels while it is crossing the curve *l* defining a curved surface along which a tomogram is made, 2) maintaining an angle of intersection of the projected X-ray R with the curve *l* at a predetermined angle, 3) synchronizing the velocity of movement B of the film surface F with the velocity of movement along the curve *l* at the point of intersection O of the projected X ray R with the curve *l*.

Figure 3:
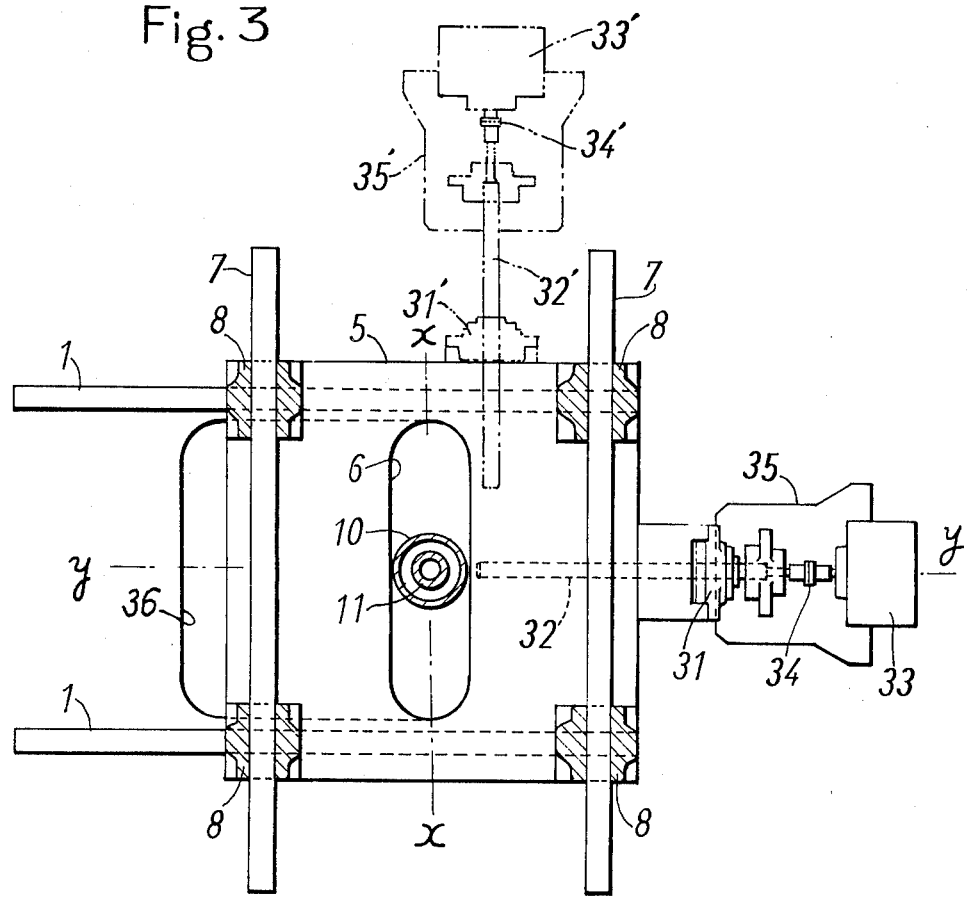
FIG. 3 is a cross sectional view taken along line III—III of FIG. 2.

A description will now be made of an apparatus for making a tomogram of arrangement of teeth according to this invention with reference to FIGS. 2 and 3. In the Figures, a bed 3 is fixed to a base 2, and rails 1 are mounted on the bed 3. Two rails 1 are parallel to each other and extend horizontally in the direction of *y*-axis. A pair of sliders 4 straddles each rail slidably. A first platform 5 is placed on these four sliders 4 and connected thereto. Accordingly, the platform 5 is enabled to move on the rails 1 in the direction of *y*-axis. And the platform is centrally formed with an opening 6 so as not to hinder the movement of a vertical hollow shaft 10 to be later described. For the same purpose as that, the base 2 is also formed with an opening 36. The platform 5 has a ball nut 31 fixed thereto and a ball screw 32 is threadedly engaged with the nut 31. The ball screw 32 is connected through a coupling 34 to the rotating shaft of a step motor 33, and the motor is fixed to a pedestal 35 mounted to the base 2. Accordingly, the platform 5 is moved on the rails 1 by rotation of the step motor 33 in the direction of *y*-axis, but the distance of movement of the platform is proportional to the quantity (angle) of rotation of the step motor that is rotated at a predetermined angle in response to the input of one pulse, and hence the distance is exactly controlled in accordance with the input pulse of the step motor 33.

On the platform 5 are fixedly provided rails 7 and two rails 7 are parallel to each other and extend horizontally in the direction of *x*-axis at right angles with the *y*-axis. A pair of sliders 8 slidably straddles each rail 7 and a second platform 9 is placed on those four sliders 8. The platform 9 is connected to the four sliders 8. The platform 9 has also a ball nut 31' fixed thereto, and a ball screw 32' is threadedly engaged with the ball nut 31'. The ball screw 32' is connected through a coupling 34' to the rotating shaft of a step motor 33' secured to a pedestal 35' of the first platform 5. Accordingly, when the step motor 33' is rotated in accordance with the pulse input thereof, the second platform 9, in response to the rotation, moves on the rails 7 fixed to the first platform 5 in the direction of *x*-axis.

The aforementioned movement of first platform 5 in the *y*-axis direction and movement of second platform 9 in the *x*-axis direction with respect to the platform 5 enable a hollow shaft 10 mounted to the center of second platform 9 to move to any desired position in the horizontal plane and giving inpulses according to a suitable control program to the step motors 33 and 33' respectively enables the shaft 10 to move along any curve (in the horizontal plane).

Inside the hollow shaft 10 is held a vertical shaft 11 in two upper and lower bearings 12, the shaft having an arm 17 secured thereto at the lower end. The shaft 11 has a spiroid gear 13 fixed thereto at the upper end, and a spiroid pinion 14 mates with the gear 13. The spiroid pinion 14 is fixed to the rotating shaft of a step motor 15 and enclosed with a gear box 16. Rotation of the step motor 15 is reduced in speed by the spiroid pinion 14 and spiroid gear 13 and transmitted to the shaft 11 to thereby turn the shaft 11 around the axis thereof. The angle of rotation of the shaft 11 is proportional to the quantity of rotation of the step motor 15 and is positively controlled in accordance with the input pulse of the step motor 15. An arm 17 is fixed by a set-bolt 18' to the lower end of the shaft 11. The arm 17 has an X-ray tube 17 incorporated X-ray projector 18 pivotally supported by a bolt 21 at one end thereof. X ray is projected in the form of a beam long in length and short in width through a slit 20 in front of the X-ray projector 18. The arm 17 has a slit plate 22 secured to the other end thereof. The narrow incident light slit formed in the plate 22 is in an opposed relation in alignment with the projection slit 20 in front of the X-ray projector 18 and only the X-ray beam projected through the slit 20 passes through the slit in the slit plate 22. The scattering x-ray produced when X ray passes through an object is prevented by the slit plate 22 from reaching the slit in the slit plate 22. There is provided a drum 23 behind the slit plate 22, and an X-ray film 24 is stretched around the surface of the drum 22. The support arm 25 of the drum 23 is fixed to the lower end of a shaft 26 held in bearings 27 by arm 17 and extending into the arm 17. The shaft 26 has a spiroid gear 28 at the upper end thereof and is in mesh with a spiroid pinion 29 fixed to the rotating shaft of a step motor 30 mounted inside the arm 17. Rotation of the step motor 30 controlled by input pulses is reduced in speed through the spiroid pinion 29 and spiroid gear 28 and transmitted to the shaft 26 to thereby turn the drum 23 around the shaft 26. In this manner, the surface of the X-ray film 24 stretched around the drum 23 is moved relatively with respect to the incident light slit of the slit plate 22 fixed to the arm 17, and the velocity of movement of the film surface is controlled in accordance with the input pulses of the step motor 30.

As described, in the apparatus for making a tomogram of arrangement of teeth according to the invention, the X-ray tube and X-ray film device are provided in a opposed relation at both ends of the arm 17, and the relative positional relation between the two is held unchanged irrespective of the movement of the arm 17. Accordingly, when the axis of the vertical shaft 11 which supports the arm 17 is moved along any desired curve by rotation of the step motors 33 and 33', the X-ray beam projected from the X-ray tube 19 on the X-ray film 24 is also moved along the curve while transversing the curve. And furthermore, in the meantime, the angle at which the X-ray beam intersects the curve is adjusted by turning the shaft 11 around the axis thereof by the step motor 15, so that the angle of intersection can be maintained at a predetermined angle. And also, the velocity at which the surface of X-ray film 24 moves with respect to the X-ray beam, namely, with respect to the slit of the slit plate 22 depends upon the rotation of the step motor 30, and synchronization of the velocity of movement of the shaft 11 with that of the surface of the film 24 can be effected by controlling the rotation of the step motor 30 in the manner that the rotation may correspond with the velocity of movement of the shaft 11 along the curve. Accordingly, in the described apparatus according to the invention, the digital signal control means essential for the invention is carried out by four step motors 33, 33', 15 and 30, and all that is necessary is to give the required input pulses to those step motors.

A description will not be made of an example of how control input is given to the step motors. First, the shape of a dental arch is collected from a patient. The shape of the dental arch collected from the patient is compared with a multiplicity of contrast model curves printed on transparent paper so as to select that model curve from the model curves which is in the best conformity with the shape collected. As for each of those model curves, digital signals to be given to each step motor for moving the shaft 11 in the manner described and for moving the shaft around the axis thereof and for moving the surface of film and beforehand calculated by an electronic computer and recorded on a perforated tape or magnetic tape as a program. Accordingly, a program corresponding to the model curve selected in making a tomogram of arrangement of teeth of the patient is caused to be stored in the memory, and if the control pulses formed on the basis of the signals thus stored are given to each step motor as input, the motor makes positive and negative rotation as programmed. Such rotation of each step motor in response to the program moves the shaft 11 along the model curve, maintains angle of intersection of X-ray beam with the model curve at a predetermined angle, and moves the film surface 24 in synchronism with the velocity at which the shaft 11 moves along the model curve, with the result that a clear and sharp tomogram of arrangement of teeth is made on the film.

As described above, in the method and apparatus for making a tomogram of arrangement of teeth according to the invention, the shaft 11 is moved in accordance with the system of x and y coordinates at right angles with each other, but it will readily be understood that the shaft 11 may be moved in accordance with the system of polar coordinates. Also, the angle of intersection of X-ray beam with the curve is normally maintained at right angles and that is desirable, but so long as the angle of intersection is maintained at a predetermined angle, slight deviation of the angle of intersection from the right angle would not be objectionable. Furthermore, in the invention, it would not be objectionable either that, instead of the shaft 11 moving along the curve itself which defines a curved surface along which a tomogram is made, the shaft may be moved along an approximate curve having a certain proportional relation with the above curve. That movement of the shaft along the curve defining the curved surface which is defined in this specification should be constructed in such a sense of the word.

The method and apparatus for making a tomogram according to this invention has been illustrated and described with main reference to an application of the tomography of arrangement of teeth, it should however be understood that the invention is not limited to the embodiment illustrated but may generally be used in the tomography of the inner parts of a living body.

What is claimed is:

1. A method of making a tomogram comprising a) moving one shaft supporting an X-ray tube and an X-ray film along a desired curve to thereby move a long and narrow X-ray beam projected from said X-ray tube on said film while the beam is transversing said curve, b) adjusting an angle of intersection of said X-ray beam with said curve by turning said shaft around the axis thereof and maintaining said angle of intersection at a predetermined angle while said X-ray beam is being moved, and c) moving the surface of said X-ray film relatively with respect to said X-ray beam incident upon the film surface to thereby cause the X-ray beam to scan the film surface and bringing the velocity of movement of the film surface into sychronism with the velocity of movement of said shaft along said curve, and d) controlling said movement of the shaft along a desired curve, of rotation of the shaft around the axis thereof, and the velocity of said movement of the X-ray film surface respectively by digital signals.

2. A method according to claim 1 wherein said angle of intersection of the X-ray beam with the curve is maintained at substantially right angles.

3. A method according to claim 1 wherein said curve represents the shape of a dental arch.

4. A method according to claim 1 wherein said movement of the shaft along the curve, said angle of rotation of the shaft around the axis thereof, and velocity of movement of the X-ray film surface are respectively controlled in accordance with the digital control program beforehand prepared.

5. A method according to claim 4 wherein one model curve which is in the best conformity with the shape of the dental arch collected from the patient is selected from a group of model curves beforehand prepared and the digital control as to said one model curve is carried out in accordance with the program beforehand prepared.

6. An apparatus for making a tomogram characterized in that the apparatus includes an elongated support member and one vertial shaft supporting member thereon, said elongated support member supporting an X-ray projector adapted to project a long and narrow X-beam, and a film device for receiving said X-ray beam in an opposed relation at both ends thereof, a means for moving said vertical shaft along a desired curve, said means being driven by digital signals, a means for turning said shaft around the axis thereof, said means being intended for maintaining the angle of intersection of said X-ray beam with said curve at a predetermined angle and being driven by digital signals, and a means for moving the surface of the X-ray film inside said film device in synchronism with the velocity of movement of said shaft along the curve, said means being driven by digital signals.

7. An apparatus according to claim 6 wherein said means for moving the vertical shaft supporting said elongated support member comprises a first horizontal platform movable on a horizontal base in a certain direction, a second horizontal platform movable on said first platform in a direction at right angles with the direction of movement of the first platform, a drive means for moving said first platform, and a drive means for moving said platform, said vertical shaft being secured to said second platform.

8. An apparatus according to claim 7 wherein said drive means for moving the first platform comprises a ball nut fixed to the first platform, a ball screw threadedly fitted into said ball nut, and a step motor fixed to the base for turning said ball screw.

9. An apparatus according to claim 7 wherein said drive means for moving said second platform comprises a ball nut fixed to the second platform, a ball screw threadedly fitted into said ball nut, and a step motor fixed to said second platform.

10. An apparatus according to claim 6 wherein said means for turning said vertical shaft supporting the elongated support member around the axis thereof comprises a step motor and a rotation transmission device for transmitting the rotation of said step motor to said vertical shaft.

11. An apparatus according to claim 6 wherein said means for moving the surface of the X-ray film comprises a step motor, a shaft rotated by said step motor to turn around the axis thereof, and a drum turning around said shaft, said X-ray film being stretched around the surface of the drum.

* * * * *

UNITED STATES PATENT AND TRADEMARK OFFICE
CERTIFICATE OF CORRECTION

PATENT NO. : 4,039,837
DATED : August 2, 1977
INVENTOR(S) : Sadayasu Onta et al.

It is certified that error appears in the above-identified patent and that said Letters Patent are hereby corrected as shown below:

Claim 1
Column 6, line 61: insert the word --angle-- before the first word "of".

Claim 4
Column 7, line 3: insert the word --said-- before the word "velocity".

Claim 6
Column 7, line 16: delete "vertial" and insert therefor --vertical--.

Column 7, line 16: insert the phrase --said support-- before the word "member".

Column 7, line 19: delete "X-Beam" and insert therefor --X-ray beam--.

Claim 7
Column 8, line 7: insert the word --second-- before the word "platform".

Signed and Sealed this

First Day of November 1977

[SEAL]

Attest:

RUTH C. MASON
Attesting Officer

LUTRELLE F. PARKER
Acting Commissioner of Patents and Trademarks